United States Patent
Scheker (10) Patent No.: US 9,962,261 B1
(45) Date of Patent: May 8, 2018

(54) PROSTHESIS INCLUDING BALL AND SOCKET ARRANGEMENT

(71) Applicant: Aptis Medical, LLC, Glenview, KY (US)

(72) Inventor: Luis Roman Scheker, Glenview, KY (US)

(73) Assignee: Aptis Medical, LLC, Glenview, KY (US)

( * ) Notice: Subject to any disclaimer, the term of this patent is extended or adjusted under 35 U.S.C. 154(b) by 903 days.

(21) Appl. No.: 13/655,807

(22) Filed: Oct. 19, 2012

(51) Int. Cl.
*A61F 2/38* (2006.01)
*A61F 2/30* (2006.01)
*A61F 2/42* (2006.01)

(52) U.S. Cl.
CPC .............. *A61F 2/30* (2013.01); *A61F 2/3804* (2013.01); *A61F 2/4241* (2013.01); *A61F 2/4261* (2013.01); *A61F 2002/30649* (2013.01); *A61F 2220/0025* (2013.01)

(58) Field of Classification Search
CPC .......... A61F 2002/30649; A61F 2/4003; A61F 2002/4003; A61F 2/3804; A61F 2002/3804; A61F 2/4261; A61F 2002/4261; A61F 2/4241; A61F 2002/4241; A61F 2002/30654
USPC ...................... 623/21.11–21.14, 20.11–20.13, 623/21.15–21.17, 23.4
See application file for complete search history.

(56) References Cited

U.S. PATENT DOCUMENTS

| | | | |
|---|---|---|---|
| 1,728,490 A | 9/1929 | Harley | |
| 2,422,302 A | 6/1947 | Horn | |
| 3,837,008 A | 9/1974 | Bahler et al. | |
| 3,889,299 A | 6/1975 | Osborne et al. | |
| 4,003,095 A | 1/1977 | Gristina | |
| 4,194,250 A * | 3/1980 | Walker | 623/23.39 |
| 4,229,840 A * | 10/1980 | Gristina | 623/21.13 |
| 4,707,771 A | 11/1987 | Van Duyn et al. | |
| 5,961,516 A * | 10/1999 | Graf | 606/256 |
| 8,052,757 B1 | 11/2011 | Scheker | |
| 8,425,605 B2 * | 4/2013 | Zielinski | 623/17.11 |
| 2007/0135919 A1 * | 6/2007 | Aebi et al. | 623/17.11 |
| 2010/0256770 A1 * | 10/2010 | Hakansson et al. | 623/21.16 |

FOREIGN PATENT DOCUMENTS

| | | |
|---|---|---|
| DE | 3216111 | 11/1983 |
| FR | 2863866 B1 * | 12/2003 |
| WO | WO 2007047230 A2 * | 4/2007 |

* cited by examiner

*Primary Examiner* — David H Willse
*Assistant Examiner* — Javier Blanco
(74) *Attorney, Agent, or Firm* — Duncan Galloway Egan Greenwald; Theresa Camoriano; Guillermo Camoriano (57) ABSTRACT

A two-piece socket for a ball-and-socket arrangement, including a base and a cap. The socket includes a leg on one of the cap or base of the socket and a receiving groove on the other of the cap or base of the socket, wherein there is at least one opening in the leg which lines up with a corresponding opening in the groove for a fastener to extend through these openings to releasably secure the cap to the base of the socket. The orientation of the fastener is such that the fastener is under shear loading when the cap is pulled apart from the base.

9 Claims, 9 Drawing Sheets

PROSTHESIS INCLUDING BALL AND SOCKET ARRANGEMENT

BACKGROUND

The present invention relates to a prosthesis that includes a ball-and-socket arrangement. In particular, it includes a socket that includes a base and cap to capture a "ball", wherein the base and the cap of the socket are releasably secured by a fastener.

SUMMARY

The prosthesis includes a first body, including a ball, and a second body, including a base and a cap which secures to the base. The base and cap each have an inner surface and an outer surface, and the inner surfaces of the base and cap together define a socket which is sized and shaped to receive the ball and support the ball for rotation relative to the second body. One of the inner and outer surfaces of the base defines a first groove, and the cap has a first leg, which is received in the first groove. The first leg defines a first leg opening having an axis extending in a cross-wise direction that is cross-wise to the direction in which the leg projects into the groove, and the base defines a base opening which is aligned with the first leg opening when the first leg is received in the first groove. A pin is received in the first leg opening and the base opening and extends in the cross-wise direction to secure the cap and base members together so that when forces are applied to attempt to slide the leg back out of the groove, those forces put the pin in shear, which provides a very secure connection.

DESCRIPTION

Figure 1:
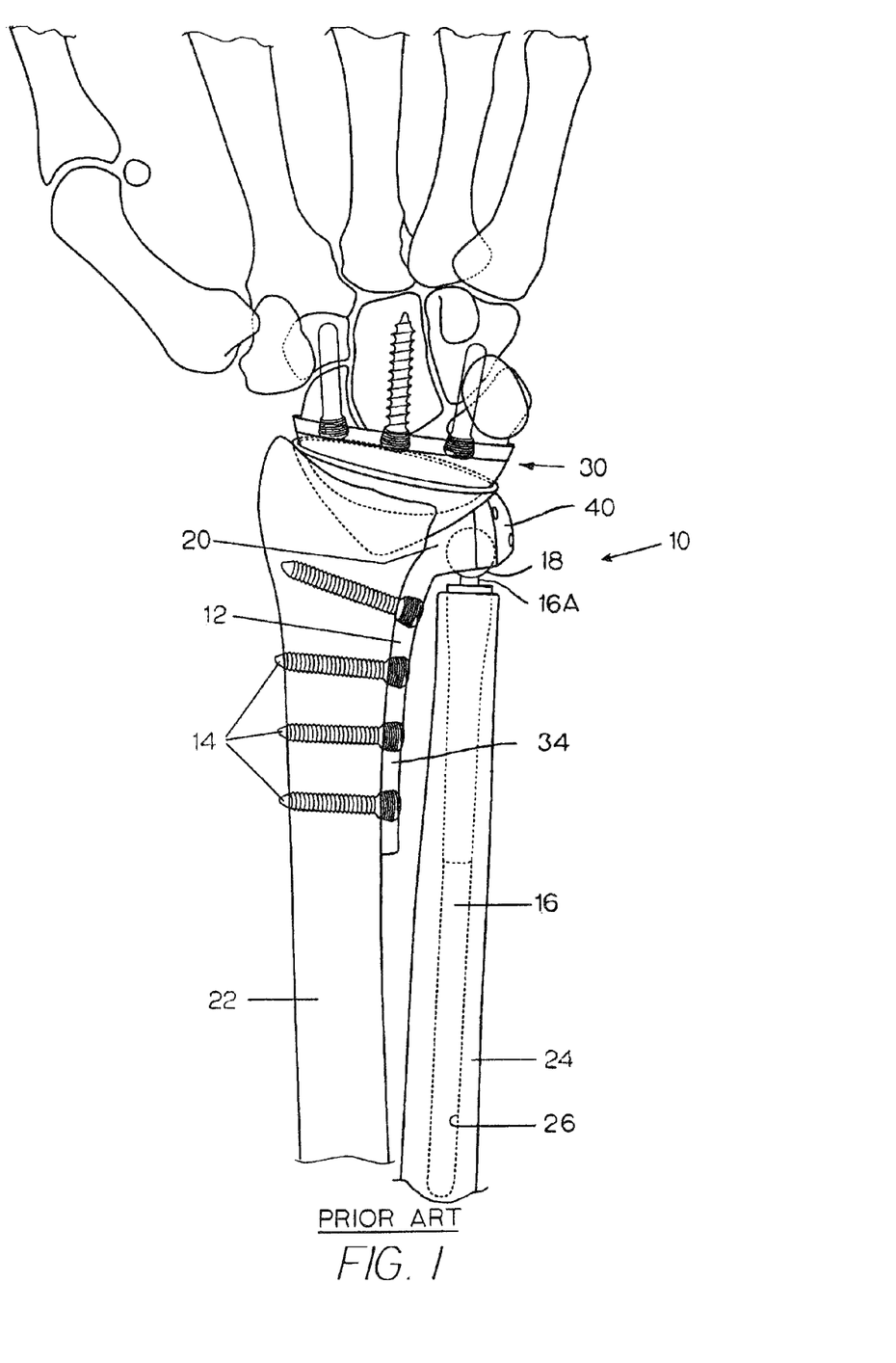
FIG. 1 is a front view of a prior art wrist prosthesis installed on a human skeleton.
Figure 2:
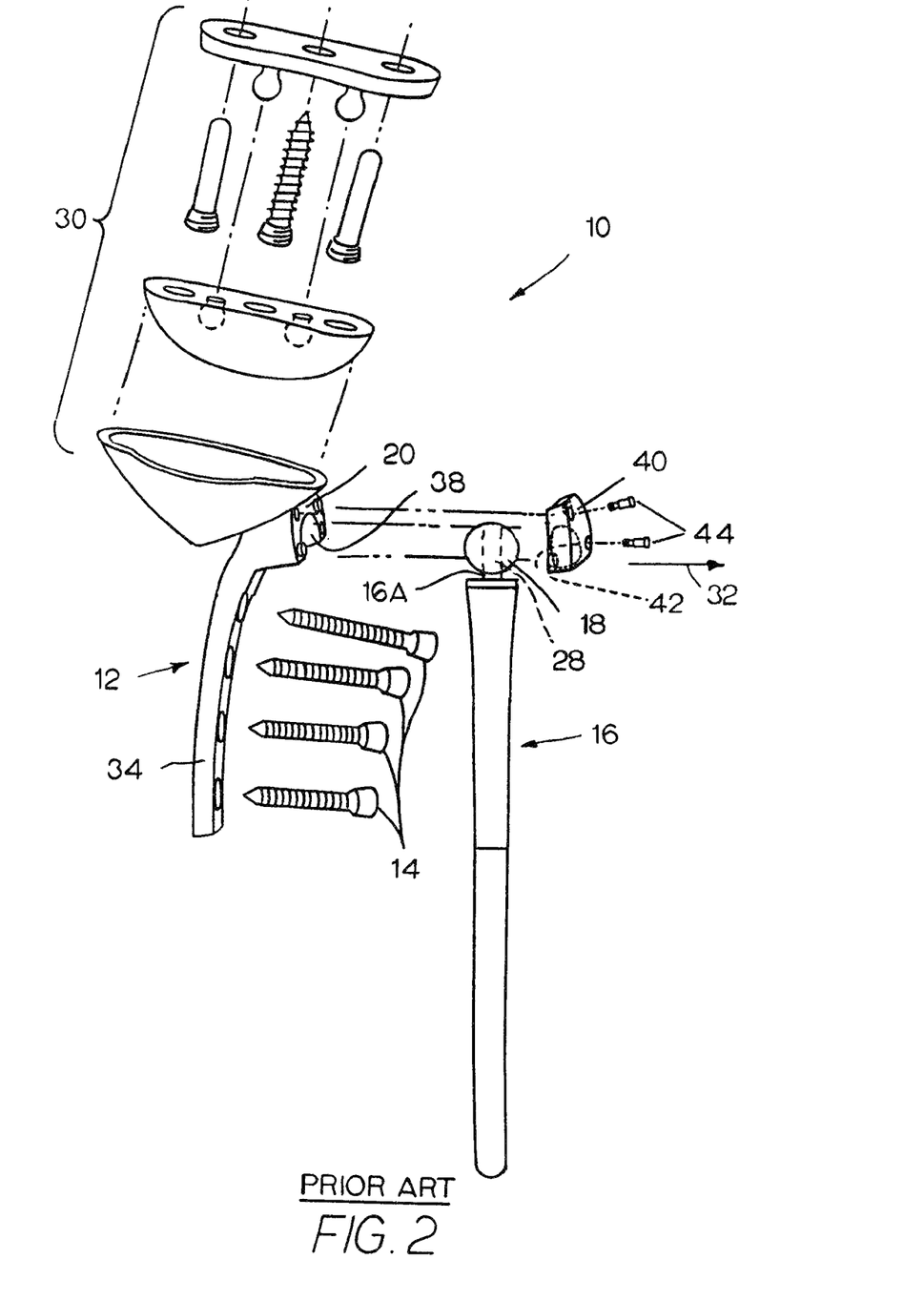
FIG. 2 is an exploded perspective view of the prior art wrist prosthesis of FIG. 1.

FIGS. 1 and 2 show a wrist prosthesis 10, as described in U.S. Pat. No. 8,052,757, "Combined total wrist and total distal radioulnar joint prosthesis", issued Nov. 8, 2011, which is hereby incorporated herein by reference. The wrist prosthesis 10 includes a radial brace body 12, which is secured to the radius bone 22 with a plurality of screws 14. Also included is an ulnar brace body 16, which is secured to the ulna bone 24, typically via a press fit into the medullary cavity 26 of the ulna 24. In addition to (or instead of) the press fit, the brace body 16 may be cemented, adhered, or secured by other means to the ulna 24.

The ulnar brace body 16 is essentially a shaft, symmetrical about a central axis. A spherical ball 18 is mounted onto the shaft 16 at one end. The ball 18 has a bore 28 (See FIG. 2) along its diameter which receives a reduced cross-section end portion 16A of the shaft 16. The ball 18 is free to pivot about the axis of the shaft 16 and to translate up and down along the central axis relative to the shaft 16.

As shown best in FIG. 2, the radial brace body 12 includes a base portion 20, which has an inner surface 38 that defines a partial spherical cavity or socket. The cap 40 has an inner surface 42, which also defines a partial spherical cavity or socket. When the is secured to the base 20 by means of screws 44, the inner surfaces 38, 42 together define a spherical socket which is sized and shaped to receive the ball 18 and to support the ball 18 for rotation. The spherical ball 18 of the ulnar brace body 16 is trapped in the partial spherical cavity formed by the base portion 20 and cap 40 and is free to swivel within and bear against the surface of that cavity, in order to support the radius 22 relative to the ulna 24 for pronation and supination of the forearm and for the bearing of weight. The bearing surface 38 is nearly in the position of the sigmoid notch of the original radius, and the ball 18 is nearly in the position of the ulna head of the original ulna, so the joint provides the same relative positions of the radius and ulna throughout the entire pronation and supination of the forearm as would have been provided by the original intact joint. This means both that the axes of the radius 22 and ulna 24 are in the same relative positions and that the longitudinal position of the joint along the axes of both bones is in the same relative position as it would have been in the original joint. The socket has a smooth, nearly continuous surface to provide for smooth rotation of the ball in the socket.

The socket ensures that the ball 18 of the ulnar brace 16 will remain engaged with the radial brace 12 so it can bear against the bearing surfaces 38, 42 to provide the desired support. The socket essentially replaces the function of the ligaments that originally held the radius in position relative to the ulna head.

The base 20 also has a mounting leg 34, projecting away from the socket, for mounting the socket to the radius bone 22 via the screws 14.

When the ball 18 bears against the bearing surface 42, it acts to push the cap 40 away from the base 20, in the axial direction of the screws 44, as shown by the arrow 32 (See FIG. 2), which places the screws 44 in tension and depends upon the engagement of the screw threads to hold the assembly together. Repeated thrusts of the ball 18 on the bearing surface 42 due to loading and unloading of the wrist may result in failure of the screws 44 or in undesirable unthreading of these screws 44. Of course, a solution to this problem could be to glue, or otherwise permanently secure, the screws 44 to the cap 40 and/or to the base 20 so they will not inadvertently come unscrewed. However, this is undesirable, because it would hamper the ability of a surgeon to remove the cap 40 from the base 20 at some later time in order to replace a worn ball 18.

Figure 3:
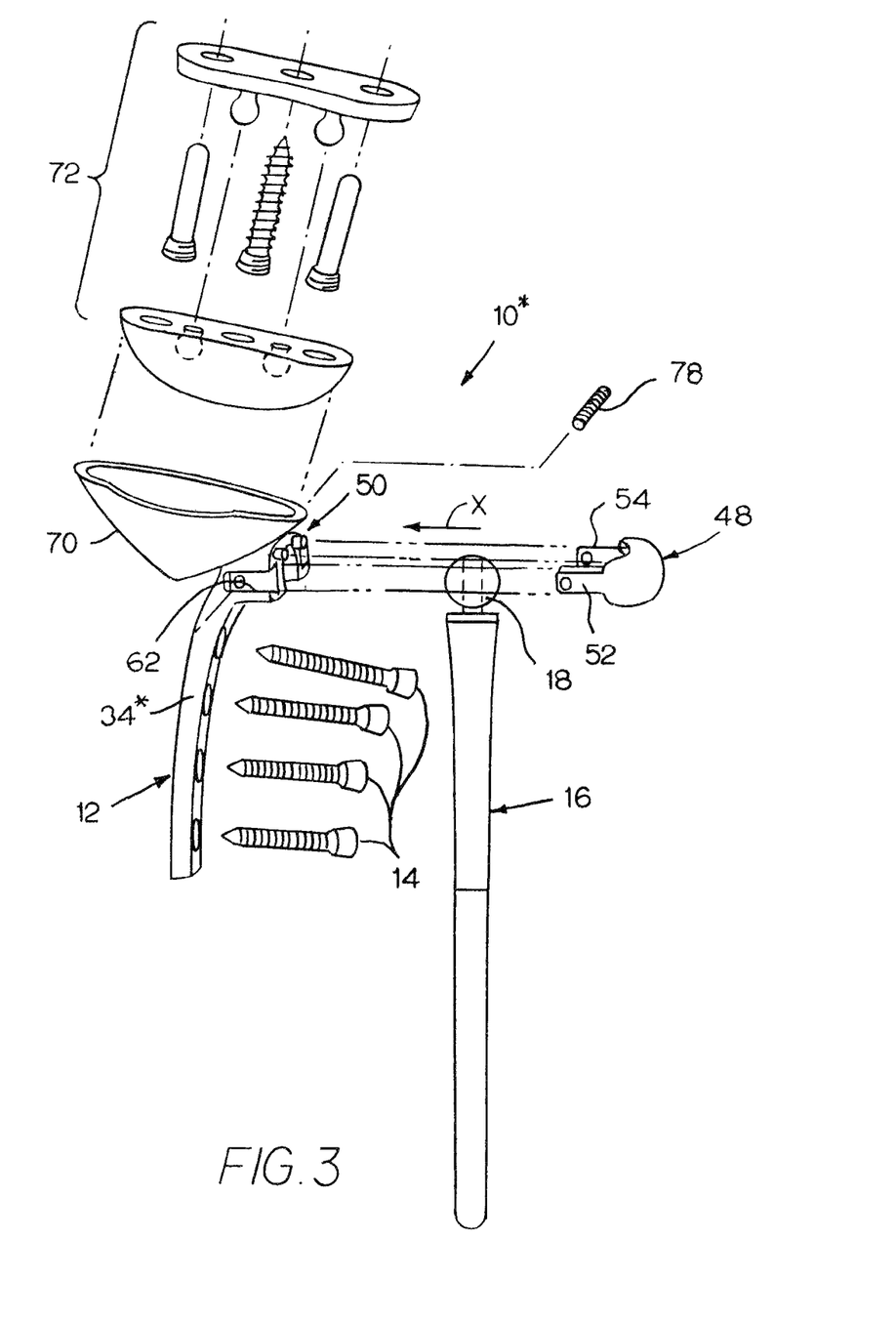
FIG. 3 is an exploded view of an embodiment of a wrist prosthesis, similar to that of FIG. 2, but made in accordance with an embodiment of the present invention.

FIG. 3 shows a wrist prosthesis 10* similar to what is shown in FIG. 2, but with a base and cap having a more secure assembly arrangement. This arrangement does not rely upon the engagement of the threads to hold the assembly together, because the force on the fastener pin 78 is not along the pin's axis, putting the pin in tension, as was the case in FIG. 2, but rather the force on the fastener pin 78 is across the pin's axis, putting the fastener pin 78 in shear, which makes for a much stronger, more secure connection.

Figure 4:
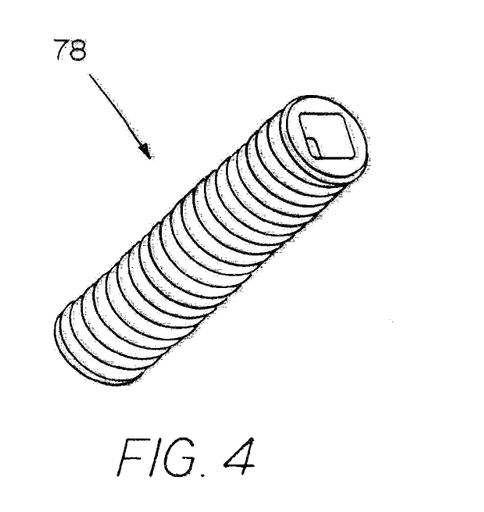
FIG. 4 is a perspective view of the pin fastener of the prosthesis of FIG. 3.
Figure 5:
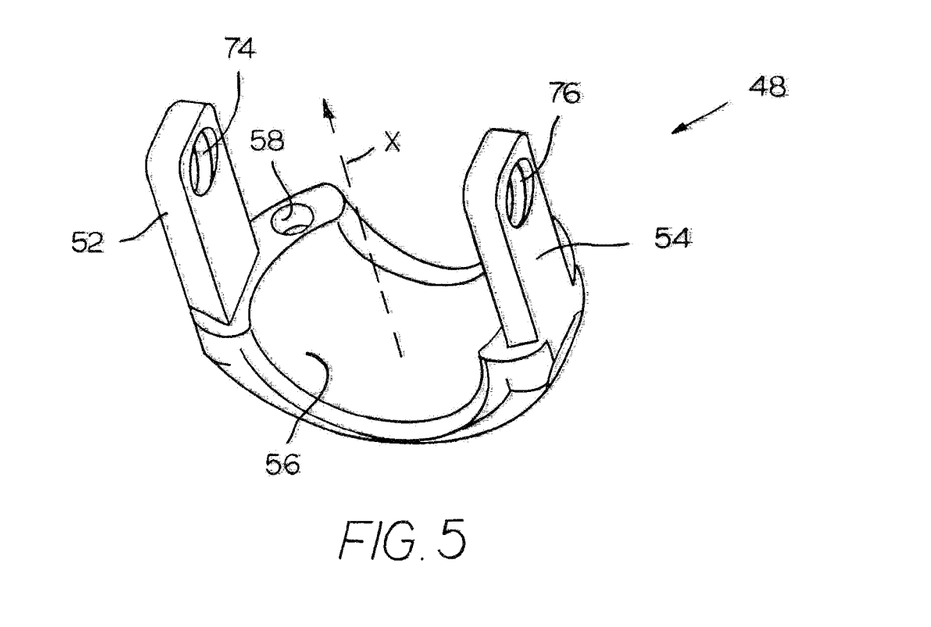
FIG. 5 is a perspective view of the cap of the prosthesis of FIG. 3.

Referring to FIG. 5, the cap 48 has an inner surface 56 that defines a partial sphere. First and second legs 52, 54, which are parallel and opposite to each other, project in a first direction "X". The legs 52, 54 of the cap 48 define internally threaded, coaxial, through openings 74, 76, respectively, which receive and mate with the threads on the fastener pin 78 (See FIGS. 3 and 4) as described in more detail later.

Figures 6, 7, 7A:
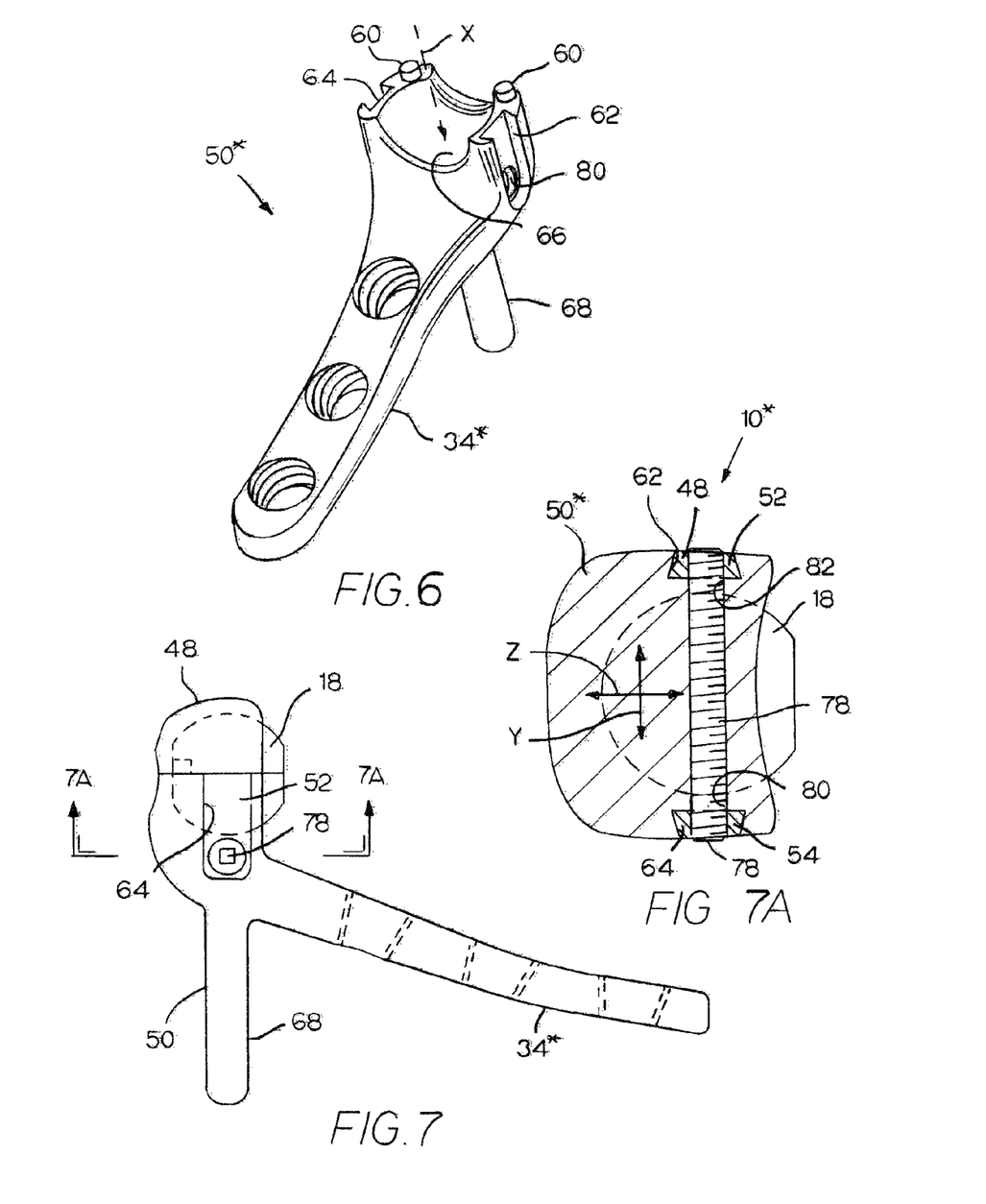
FIG. 6 is a perspective view of the base of the prosthesis of FIG. 3, but somewhat modified, with the cup 70 removed and a pin 68 added.
FIG. 7 is a side view of the prosthesis assembly incorporating the fastener, the cap of FIGS. 3 and 5, and the base of FIG. 6.
FIG. 7A is a section view along line 7A-7A of FIG. 7.

FIG. 6 shows a base 50* which is very similar to the base 50 of FIG. 3, except the cup 70 has been removed and a pin 68 has been added.

The base 50* includes a mounting leg 34* for mounting the socket on the radius bone. The base 50* has an inner surface 66, which defines a partial sphere. It also has an outer surface that defines first and second grooves 62, 64, which are parallel and opposite to each other and which extend in a first direction "X". When the cap 48 and base 50* are assembled together, with the first and second legs 52, 54 received in the first and second grooves 62, 64, the inner surfaces 56, 66 together form a socket, which is sized and shaped to receive the spherical ball 18 of the prosthesis 10* and to support the ball 18 for rotation. As in the prior art arrangement of FIG. 2, the socket forms a smooth, nearly continuous inner surface to provide for smooth rotation of the ball 18. The assembled base 50* and cap 48 function in essentially the same manner as the base 20 and cap 40 of FIG. 2, capturing the ball 18 and allowing the ball 18 to rotate.

The grooves 62, 64 of the base 50* define internally threaded, through openings 80, 82 (only one shown in FIG. 6 but both visible in FIG. 7A), which have an axis extending in a direction that is cross-wise to the first direction "X". These threaded openings 80, 82 receive the externally threaded fastener pin 78 (See FIGS. 3 and 4) as described in more detail later.

It should be noted that the first direction "X" of FIG. 6 is the same as the first direction "X" of FIG. 5, and is represented as well in FIG. 3 as being the direction in which the legs 52, 54 slide into the grooves 62, 64 to assemble the cap 48 and base 50* together. Of course, to disassemble the cap 48 from the base 50*, the cap 48 would be moved in the opposite direction relative to the base 50* in order to slide the legs 52, 54 out of the grooves 62, 64.

The appendage 68 shown extending from the back of the base 50* is inserted into a hole drilled in the radius bone 22 to help fix the position of the base 50* relative to the bone.

The cap 48 also defines two recesses 58 (only one is visible in FIG. 5) sized and located so as to receive mating projections 60 (See FIG. 6) on the base 50*.

FIG. 7 shows the assembly of the cap 48, the base 50*, the ball 18, and the fastener pin 78. The stem 16, which is assembled to the ball 18, is omitted for simplicity. To assemble the prosthesis 10*, the ball 18 is placed between the partial spherical cavities 56, 66, of the cap 48 and base 50*, and then the cap 48 and base 50 are brought together in the first direction "X" (See FIG. 3), wherein the legs 52, 54 of the cap 48 slide into the grooves 62, 64 respectively of the base 50* until the projections 60 are received in the recesses 58 and the through openings 74, 76 of the cap 48 are aligned with the corresponding through openings 80, 82 in the base 50*. The fastener pin 78 is then threaded through all four aligned openings 74, 80, 76, 82, with the axis of the fastener pin 78 extending cross-wise to the first direction "X". Note that the fastener pin 78 may be inserted from either side of the prosthesis 10* which allows the same prosthesis to be used for either a "left hand" application or a "right hand" application.

A closer look at FIG. 7A shows that the sides of the legs 52, 54 taper outwardly and that the sides of the grooves 62, 64, which receive the legs 52, 54, taper inwardly with a mating taper. When the legs 52, 54 are received in the grooves 62, 64, as shown in FIG. 7A, the tapered surfaces of the grooves 62, 64 partially overlie and contact the mating outer surfaces of the legs 52, 54, which prevents the legs 52, 54 from moving outwardly, in the "Y" direction, away from their respective grooves 62, 64. As soon as the legs 52, 54 are received in the grooves 62, 64, the legs 52, 54 are prevented from moving in any direction other than the X direction relative to the grooves. And once the fastener pin 78 is threaded into the prosthesis 10*, the legs 52, 54 also are prevented from moving in the first direction "X", thereby fixing the cap 48 relative to the base 50* in every direction.

Any force acting to separate the cap 48 from the base 50* in the "X" direction (the direction to slide the legs 52, 54 out of the grooves 60, 62) acts in the cross-wise direction, across the fastener pin 78, thereby applying shear forces to the fastener pin 78. This does not tend to unthread the fastener pin 78 and does not rely on the engagement of the threads to hold the parts together. Instead, it relies on the body of the fastener pin 78 itself, since, as long as the pin 78 is in place, one would have to shear the pin (cut it entirely through) in order to slide the legs 52, 54 out of their respective grooves 60, 62.

Figures 7B, 8:
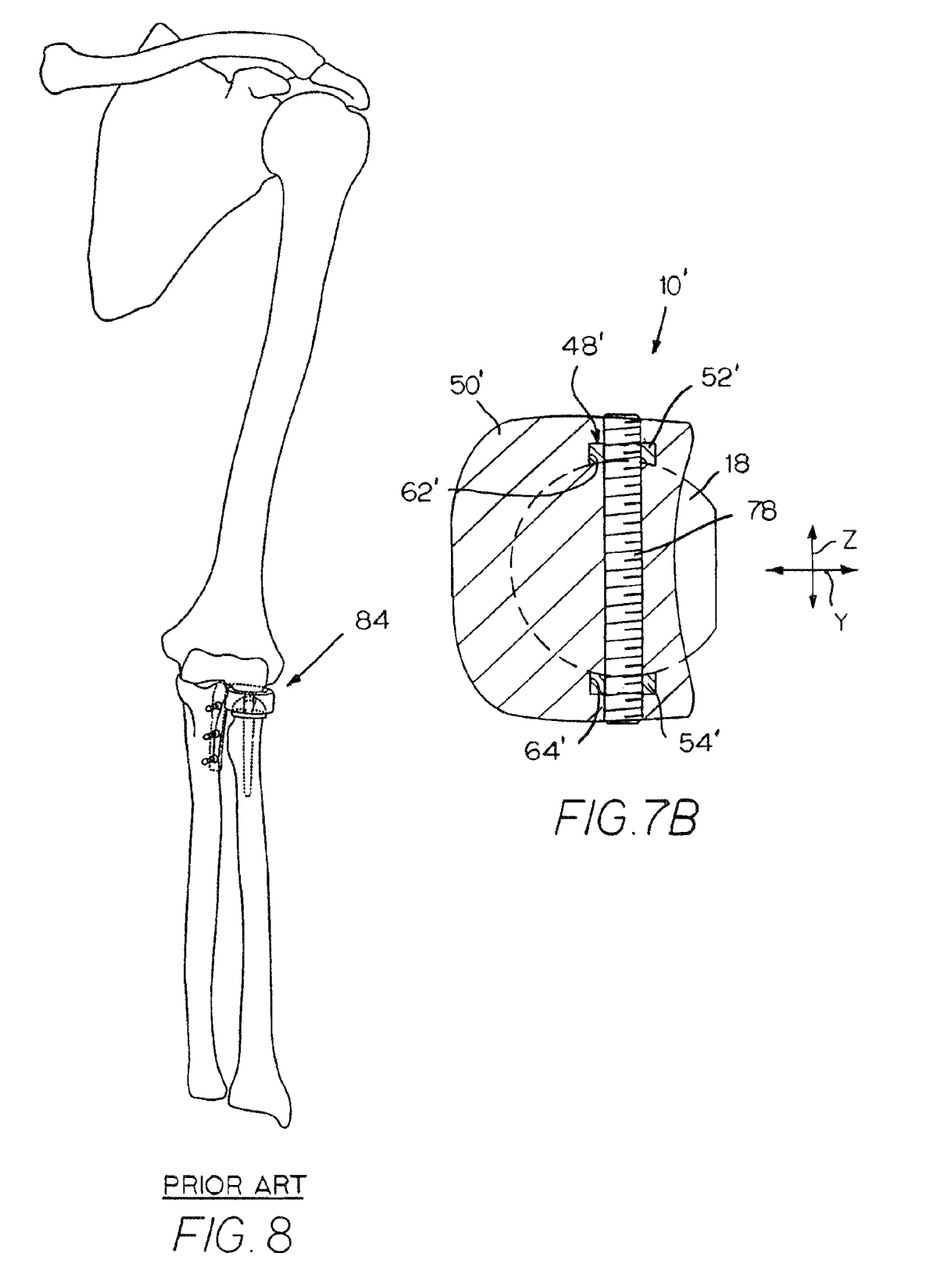
FIG. 7B is a section view, similar to that of FIG. 7A, but for an alternate embodiment.
FIG. 8 is a perspective view of a prior art elbow prosthesis installed on a human skeleton.

FIG. 7B shows a second embodiment of the prosthesis 10'. In this embodiment, the legs 52', 54' of the cap 48' are received in grooves 62', 64' formed on the inner surface of the base. In this case, the space between the legs 52', 54' is less than in the previous embodiment, and the inner surfaces of the legs 52', 54' have a partial spherical shape and become part of the socket that is in contact with the ball 18. In this case, the ball 18 prevents the legs 52', 54' from moving inwardly, and the inner surface of the cap base 50' that contacts the outer surface of the legs 52', 54' prevents the legs 52', 54' from moving apart outwardly, in the "Y" direction. The edges of the grooves 62', 64' prevent the legs from moving in the "Z" direction.

It should be noted that either of the members may be considered to be the base, with the other member being the cap, so the grooves may be placed on either member, and the legs would then be placed in the other member. In addition, it would be possible to put both a groove and a leg on the cap and a corresponding mating leg and groove on the base member.

It should also be noted that, whether the legs 52, 54 are placed on the outside of the base 50 or the cap 48, or placed on the inside of the base 50 or the cap 48, the socket has a smooth, nearly continuous surface to provide for smooth rotation of the ball in the socket. Also, in the embodiment 10* the through openings 74, 76 on the legs 52, 54 are located adjacent the mounting leg 34*, with the remainder of the outer surfaces of the base 50 and the cap 48 being smooth and nearly continuous, in order to minimize the opportunity for the prosthesis to catch on or interfere with ligaments when the prosthesis is installed. In contrast, the prior art design, shown in FIG. 2, has fasteners 44 on the outer surface of the cap 40, with recesses that could catch on ligaments.

While the present mounting arrangements for a ball-and-socket joint have been described with respect to a wrist joint, they also could be used for other ball-and-socket joints, such as the elbow and the base of the thumb. Examples of these are described briefly below.

Figure 9:
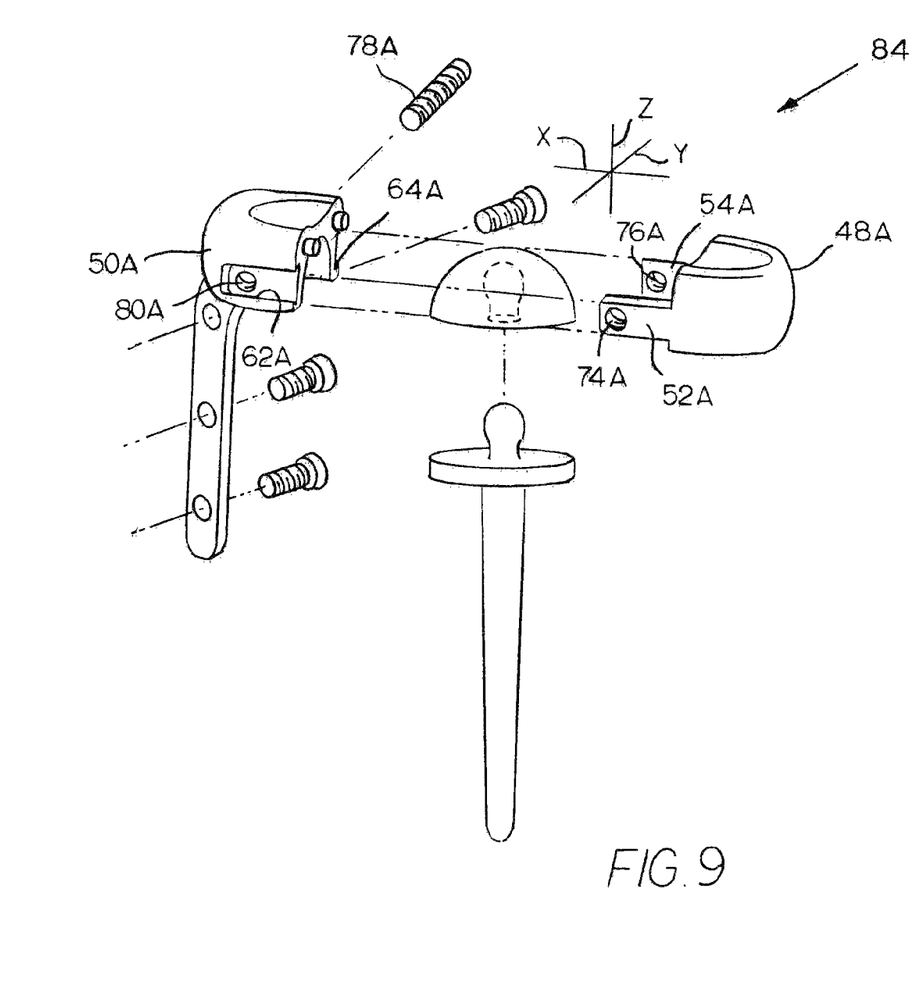
FIG. 9 is an exploded view of an elbow prosthesis made in accordance with an embodiment of the present invention to replace the elbow prosthesis of FIG. 8.

FIG. 8 shows a prior art elbow prosthesis 84, as described in U.S. Pat. No. 8,048,162, Lateral Elbow Prosthesis—Proximal Radioulnar Joint, dated Nov. 1, 2011, which is hereby incorporated herein by reference. FIG. 9 is an exploded view of an elbow prosthesis that is similar to the prosthesis of FIG. 8 but with an improved socket 84* that has a more secure connection, similar to the wrist connection described earlier. It may be seen that the cap 48A includes legs 52A, 54A which extend in the "X" direction. The base 50A defines grooves 62A, 64A which receive the legs 52A, 54A of the cap 48A. The fastener pin 78A extends in a cross-wise direction through aligned openings 80A in the base 50A, and 74A, 76A in the cap 48A to releasably secure the cap 48A to the base 50A, with the fastener pin 78A under shear loading as forces act to try to separate the cap 48A from the base 50A in the "X" direction. As with the wrist prostheses described earlier, the grooves 62A, 64A restrict the legs 52A, 54A to movement in the X direction. The legs 52A, 54A and grooves 62A, 64A have mating tapers that are the same as those shown in FIG. 7A for the wrist.

Figure 10:
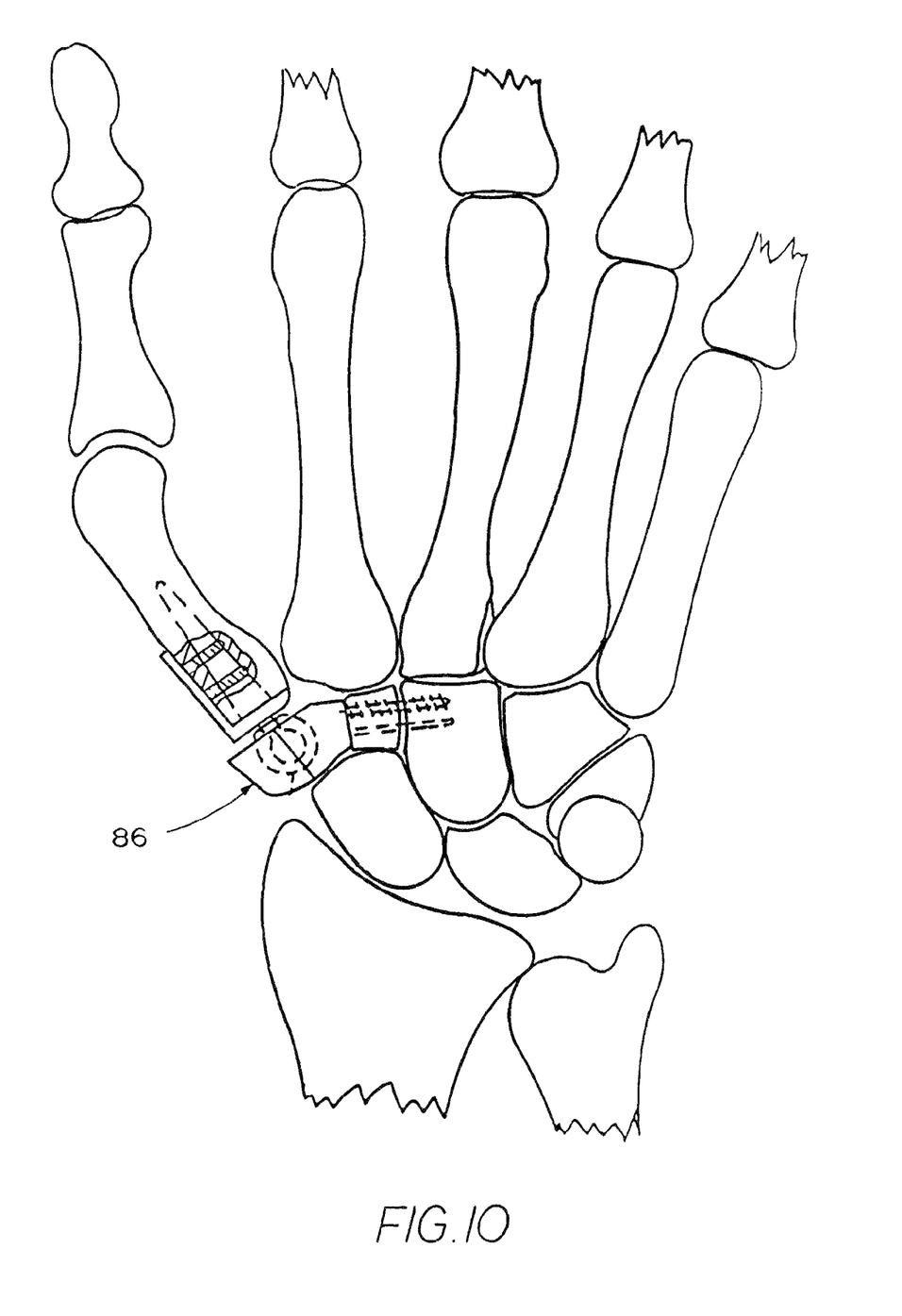
FIG. 10 is a skeletal, front view showing a thumb prosthesis installed on a human hand.
Figure 11:
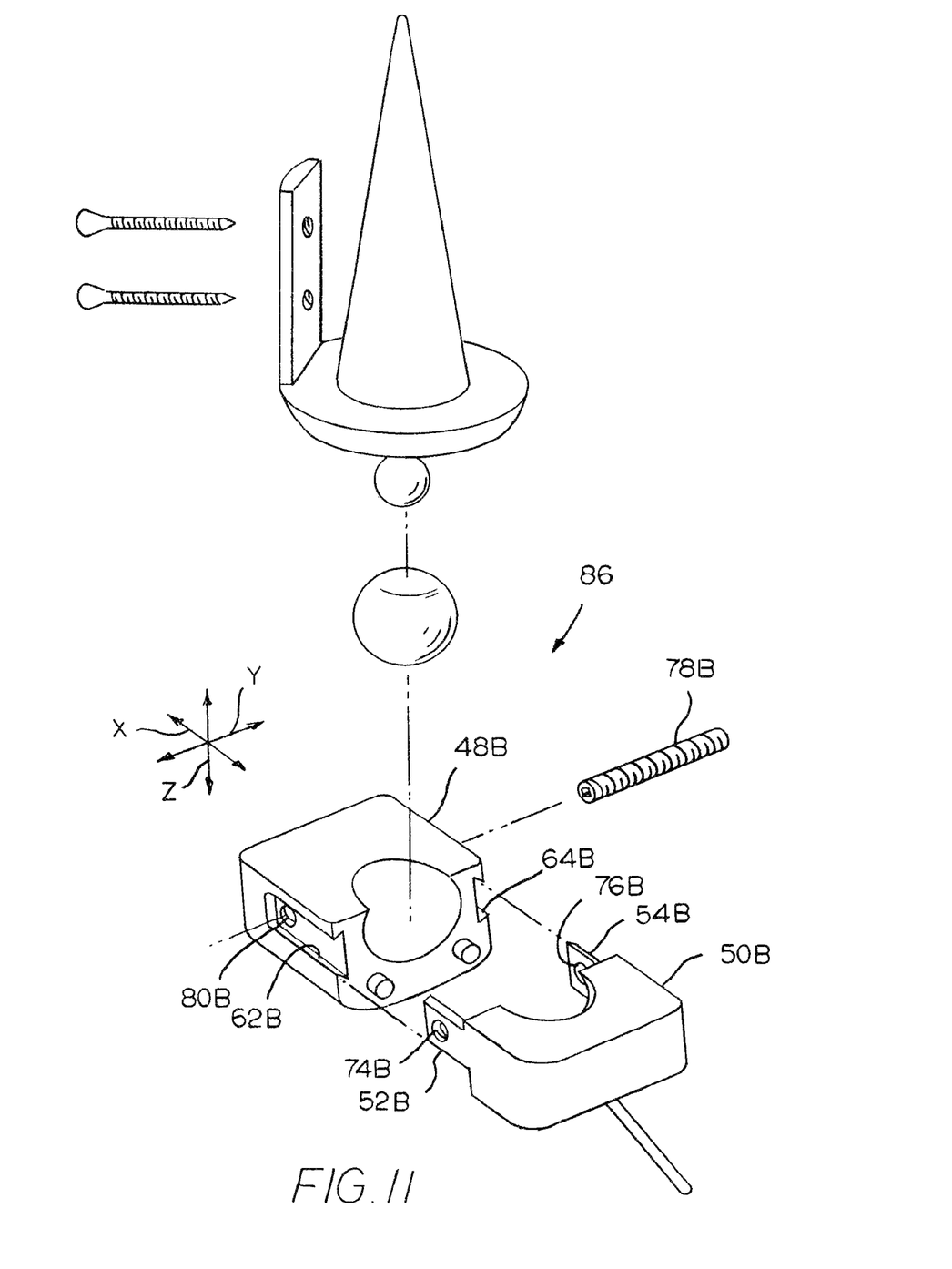
FIG. 11 is an exploded view of the thumb prosthesis of FIG. 10.

FIGS. 10 and 11 show a prosthesis 86 for the base of the thumb which uses a similar mounting arrangement for the cap and base. FIG. 11 is an exploded view of the thumb prosthesis of FIG. 10. It may be seen that the base 50B includes legs 52B, 54B which extend in the "X" direction. The cap 48B defines grooves 62B, 64B which receive the legs 52B, 54B of the base 50. The fastener pin 78B extends in a cross-wise direction through aligned openings 80B in the cap 48B, and 74B, 76B in the base 50B to releasably secure the cap 48B to the base 50B, with the fastener pin 78B under shear loading as forces act to separate the cap 48B from the base 50B in the "X" direction. The legs 52B, 54B are received in and engage the grooves 62B, 64B to restrict movement of the cap 48B relative to the base 50B to movement in the X direction. The legs 52B, 54B have tapered edges that are mated to the tapered edges of the grooves 62B, 64B and function in the same way as the mated tapered edges described earlier.

It will be obvious to those skilled in the art that modifications may be made to the embodiments described above without departing from the scope of the present invention as defined by the claims.

What is claimed is:

1. A prosthesis for replacing a mammalian joint, comprising:
    a first body, including a ball mounted on a shaft;
    a second body, including a base and a cap which secures to the base, said base and cap each having an inner surface and an outer surface, with the inner surfaces of the base and cap together defining a socket which receives and traps the ball and supports the ball for rotation relative to the second body;
    wherein one of said inner and outer surfaces of said base defines a first groove, and said cap has a first leg projecting in a first direction and being received in said first groove by sliding into said first groove in said first direction; and
    wherein said first leg defines a first leg opening having an axis extending in a direction that is cross-wise to the first direction, and said base defines a base opening which is aligned with said first leg opening when the base and cap are assembled together; and
    a pin received in said first leg opening and said base opening and extending in the cross-wise direction to secure the cap and base together so that an attempt to slide the cap and base apart from each other in the first direction applies shear forces to the pin;
    means for preventing the first leg from moving outwardly away from the first groove in the cross-wise direction when the first leg is received in the first groove;
    wherein said means for preventing the first leg from moving outwardly away from the first groove includes at least a portion of said base contacting the outer surface of the first leg;
    wherein at least one of said first leg opening and said base opening is a threaded opening, and said pin has threads which mate with corresponding threads in said threaded opening;
    and further comprising a second leg and a second groove lying parallel to and directly opposite said first leg and first groove, wherein said second leg defines a second leg opening coaxial with the first leg opening, and wherein said pin extends through the first and second leg openings and can be installed both from the first leg side of the prosthesis and from the second leg side of the prosthesis.

2. A prosthesis for replacing a mammalian joint as recited in claim 1, wherein the socket has a smooth, nearly continuous surface to provide for smooth rotation of the ball in the socket.

3. A prosthesis for replacing a mammalian joint as recited in claim 2, wherein the base defines a mounting leg projecting away from the socket for mounting the socket on a bone, the first and second leg openings are adjacent to said mounting leg, and the remainder of the outer surfaces of said base and cap are smooth and nearly continuous, in order to minimize the opportunity for the prosthesis to catch on or interfere with ligaments when the prosthesis is installed.

4. A prosthesis for replacing a mammalian joint, comprising:
    a first body, including a ball mounted on a shaft;
    a second body, including a base and a cap which secures to the base, said base and cap each having an inner surface and an outer surface, with the inner surfaces of the base and cap together defining a socket which receives and traps the ball and supports the ball for rotation relative to the second body;
    wherein one of said inner and outer surfaces of said base defines a first groove, and said cap has a first leg projecting in a first direction and being received in said first groove by sliding into said first groove in said first direction; and
    wherein said first leg defines a first leg opening having an axis extending in a direction that is cross-wise to the first direction, and said base defines a base opening which is aligned with said first leg opening when the base and cap are assembled together; and
    a pin received in said first leg opening and said base opening and extending in the cross-wise direction to secure the cap and base together so that an attempt to slide the cap and base apart from each other in the first direction applies shear forces to the pin;
    means for preventing the first leg from moving outwardly away from the first groove in the cross-wise direction when the first leg is received in the first groove;

wherein said means for preventing the first leg from moving outwardly away from the first groove includes at least a portion of said base contacting the outer surface of the first leg;

wherein the socket has a smooth, nearly continuous surface to provide for smooth rotation of the ball in the socket;

wherein one of said cap and base defines a second leg and the other of said cap and base defines a second groove, with said second leg and second groove lying parallel to and directly opposite said first leg and first groove and wherein said second leg defines a second leg opening coaxial with the first leg opening, and wherein said pin extends through the first and second leg openings and can be installed both from the first leg side of the prosthesis and from the second leg side of the prosthesis;

wherein the base defines a mounting leg projecting away from the socket for mounting the socket on a bone, the first and second leg openings are adjacent to said mounting leg, and the remainder of the outer surfaces of said base and cap are smooth and nearly continuous, in order to minimize the opportunity for the prosthesis to catch on or interfere with ligaments when the prosthesis is installed; and wherein at least one of said first leg opening and said base opening is a threaded opening, and said pin defines threads which mate with corresponding threads in said threaded opening.

5. A prosthesis for replacing a mammalian joint as recited in claim 4, wherein each of said first and second grooves lies on the inner surface of the respective cap or base member on which the respective groove is located.

6. A prosthesis for replacing a mammalian joint as recited in claim 4, wherein each of said first and second grooves lies on the outer surface of the respective cap or base on which the respective groove is located, and wherein each of said first and second grooves has edges that overlie the outer surface of the respective leg that is received in the respective groove when the legs are inserted into the grooves.

7. A prosthesis for replacing a mammalian joint as recited in claim 4, wherein said prosthesis is a replacement for the joint at the base of the thumb.

8. A prosthesis for replacing a mammalian joint as recited in claim 4, wherein said prosthesis is a replacement for the wrist joint.

9. A prosthesis for replacing a mammalian joint as recited in claim 4, wherein said prosthesis is a replacement for the elbow joint.

* * * * *